US00PP17019P2

(12) United States Plant Patent
Kapiteijn

(10) Patent No.: US PP17,019 P2
(45) Date of Patent: Aug. 22, 2006

(54) ***ZANTEDESCHIA* PLANT NAMED 'CAPTAIN CUPIDO'**

(50) Latin Name: ***Zantedeschia* sp.**
Varietal Denomination: Captain Cupido

(75) Inventor: Antonius S. J. Kapiteijn, Anna Paulowna (NL)

(73) Assignee: Kapiteijn Breeding BV, Anna Paulowna (NL)

( * ) Notice: Subject to any disclaimer, the term of this patent is extended or adjusted under 35 U.S.C. 154(b) by 84 days.

(21) Appl. No.: 11/018,174

(22) Filed: Dec. 21, 2004

(30) Foreign Application Priority Data

May 27, 2004 (EP) ..... 20040986

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Mark P. Bourgeois

(57) ABSTRACT

A new cultivar of *Zantedeschia* plant named 'Captain Cupido' that is characterized by green leaves and yellow-green colored flowers.

1 Drawing Sheet

Botanical classification: *Zantedeschia* sp.
Variety denomination: 'Captain Cupido'.

BACKGROUND OF THE INVENTION

The present invention relates to a new and distinct cultivar of *Zantedeschia* plant botanically known as *Zantedeschia* sp. and herein after referred to by the cultivar name 'Captain Cupido'.

'Captain Cupido' is a hybrid that originated from the induced hybridization of the female or seed parent *Zantedeschia* sp. Zaailing 60 (not patented) and the male or pollen parent *Zantedeschia* sp. Zaailing 05 (not patented). The cultivar 'Captain Cupido' was selected by the inventor in June of 2000 as a single plant within the progeny of the stated cross in Breezand, The Netherlands.

Asexual reproduction by tissue culture of the new cultivar 'Captain Cupido' was first performed in January of 2001 in De Goorn, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Zantedeschia cultivar 'Captain Cupido'*.

1. *Zantedeschia* 'Captain Cupido' exhibits green leaves.
2. *Zantedeschia* 'Captain Cupido' exhibits yellow-green colored flowers.
3. *Zantedeschia* 'Captain Cupido' exhibits strong flowers.

The closest comparison cultivar is *Zantedeschia* 'Captain Eskimo'. The new cultivar 'Captain Cupido' is distinguishable from 'Captain Eskimo' by the following characteristics:

1. 'Captain Cupido' produces more flowers than 'Captain Eskimo'.
2. 'Captain Cupido' has narrower leaves than 'Captain Eskimo'.

3. 'Captain Cupido' has green leaves. The leaves of 'Captain Eskimo' are spotted.
4. 'Captain Cupido' has smaller flowers than 'Captain Eskimo'.

The new cultivar 'Captain Cupido' is distinguishable from the male parent *Zantedeschia* Zaailing 05 in having broader leaves. The new cultivar 'Captain Cupido' is distinguishable from the female parent *Zantedeschia* Zaailing 60 in having yellow-green colored flowers and green leaves. Zaailing 60 has pink flowers and spotted leaves.

BRIEF DESCRIPTION OF THE DRAWING

The accompanying photograph illustrates the distinguishing traits of *Zantedeschia* 'Captain Cupido'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Zantedeschia* cultivar named 'Captain Cupido'. Data was collected in Bleiswijk, The Netherlands from 24 month old greenhouse grown plants in 17 cm. containers. The time of year was Fall and the average temperature was 24 degrees Centigrade during the day and 17 degrees Centigrade at night. No photoperiodic treatments were used. Gibberallic Acid was used to induce flowering. Color determinations are in accordance with The Royal Horticultural Society Colour Chart 2001 edition, except where general color terms of ordinary dictionary significance are used. The growing requirements are similar to the species. 'Captain Cupido' has not been tested under all possible conditions and phenotypic differences may be observed with variations in environmental, climatic, and cultural conditions, however, without any variance in genotype.

Botanical classification: *Zantedeschia* sp. 'Captain Cupido'.
Use: Ornamental.
Parentage: 'Captain Cupido' is a hybrid plant that resulted from the induced hybridization of the following parent plants:
*Female parent.*—*Zantedeschia* sp. Zaailing 60.
*Male parent.*—*Zantedeschia* sp. Zaailing 05.
Vigor: Moderate.
Growth rate: Moderate.
Growth habit: Freely clumping, bushy and dense foliage.
Plant shape: Rounded with arching leaves.
Suitable container size: 14 cm diameter container.
Height: Average 30 cm to top of leaf plane, 36 cm to top of inflorescences.
Width: Average 47 cm in width.
Hardiness: USDA Zone 10.
Propagation: Tissue Culture.
Time to initiate roots: Approximately 540 days to produce roots on an initial cutting at between 17–25 degrees Centigrade.
Crop time: 720 days.
Root system: Fine and fibrous.
Stem: No stems, Leaves grow directly from base, Average 10 clumps.
Foliage:
*Texture.*—Smooth, slightly leathery.
*Leaf arrangement.*—Alternate.
*Compound or single.*—Single.
*Leaf shape.*—Narrow elliptic to lanceolate.
*Leaf apex.*—Apiculate.
*Leaf base.*—Attenuate.
*Leaf length.*—Average 18.6 cm in length.
*Leaf width.*—4.4 cm in width.
*Quantity of leaves per clump.*—Average 4.
*Pubescence.*—Absent.
*Leaf margin.*—Entire, wavy.
*Vein pattern.*—Pinnate.
*Young leaf color* (*upper surface*).—143A.
*Young leaf color* (*lower surface*).—144A.
*Mature leaf color* (*upper surface*).—137A.
*Mature leaf color* (*lower surface*).—143A to 144A.
*Vein color* (*lower surface*).—144A.
*Vein color* (*upper surface*).—137A.
*Leaf attachment.*—Petiolate.
*Petiole dimensions.*—Average 12.4 cm in length and 4 mm in diameter.
*Petiole aspect.*—Round.
*Petiole texture.*—Smooth.
*Petiole surface.*—Slightly glossy.
*Petiole color.*—143A to 144A with a base 144A to 144B and brown stripes 200D.
*Petiole sheath dimensions.*—Average 6.2 cm in length and 5 mm in diameter.
*Petiole sheath color.*—145C to 145C with brown stripes 200D.
*Durability of foliage to stress.*—Moderate to high.
Inflorescence:
*Inflorescence arrangement.*—Spathes with spadices held above the foliage on erect peduncles arising from the petiole sheath.
*Flowering habit.*—Continuous.
*Quantity of spathes per plant.*—18.
*Natural flowering season.*—Summer.
*Time to flower or response time.*—18 months.
*Fragrance.*—Absent.
*Self-cleaning or persistent.*—Persistent.
*Flower longevity.*—Lasts approximately 8 months on plant.
*Spathe aspect.*—Concave, strongly cupped with wavy margin, spadices columnar, slightly tapering toward the top.
*Spathe dimensions.*—Average 9.1 cm in length, 5.3 cm in width and 6.5 cm in depth.
*Spathe texture.*—Glabrous, slightly leathery.
*Spathe shape.*—Broad ovate.
*Spathe margin.*—Entire, wavy.
*Spathe apex.*—Mucronate.
*Spathe base.*—Cuneate.
*Spathe color when opening* (*front side*).—145C, tip greener; 144A to 144B, with a greyed-purple to brown basal spot; in between N186C and 200A.
*Spathe color when opening* (*back side*).—144C to 144D, lighter towards the margins; 145C to 145D.
*Spathe color when fully opened* (*front side*).—145C, tip greener; 144A, with a purple to greyed-purple basal spot; in between N79B and N186C.
*Spathe color when fully opened* (*back side*).—144C, darker towards the base; 144A.
*Spathe color fading to.*—144B to 144C, darker towards the base; 144A, with a purple to greyed-purple basal spot; in between N79B and N186C on the inside.
*Spadix shape.*—Columnar, slightly tapered, arising from top of peduncle, pistilate flowers located at the base of the spadix, staminate flowers located at the top of the spadix.
*Spadix tip.*—Obtuse.
*Spadix base.*—Obtuse.
*Spadix dimensions.*—Average 3.2 cm in length and 6.5 mm in diameter.
*Spadix color when opening.*—Pistilate flowers 157D, staminate flowers 4B.
*Spadix color when fully opened.*—Pistilate flowers 157D, staminate flowers 13C.
*Quantity of flowers per spadix.*—Average pistilate flowers 24, staminate flowers 350.
*Spadix flower shape.*—Pistilate flowers rounded, staminate flowers irregular, narrow oblong.
*Spadix flower dimensions.*—Pistilate flowers 2.5 mm in diameter and 1 mm in depth, staminate flowers 1.0 mm in diameter and 0.5 mm in depth.
Reproductive organs:
*Anther color.*—13C.
*Amount of pollen.*—Low.
*Pollen color.*—8D.
*Stigma color.*—22A.
*Ovary color.*—155D.
Peduncle:
*Peduncle dimensions.*—Average 21.8 cm in length and 6.0 mm. in diameter.
*Peduncle angle.*—20 degrees.
*Peduncle color.*—145A, lighter at the base 145D.
*Peduncle strength.*—Moderate.
Seed: Seed production has not been observed.
Disease and insect resistance: Plants of the new *Zantedeschia* have not been observed for disease or insect resistance.

What is claimed is:

1. A new and distinct variety of *Zantedeschia* plant named 'Captain Cupido' as described and illustrated.

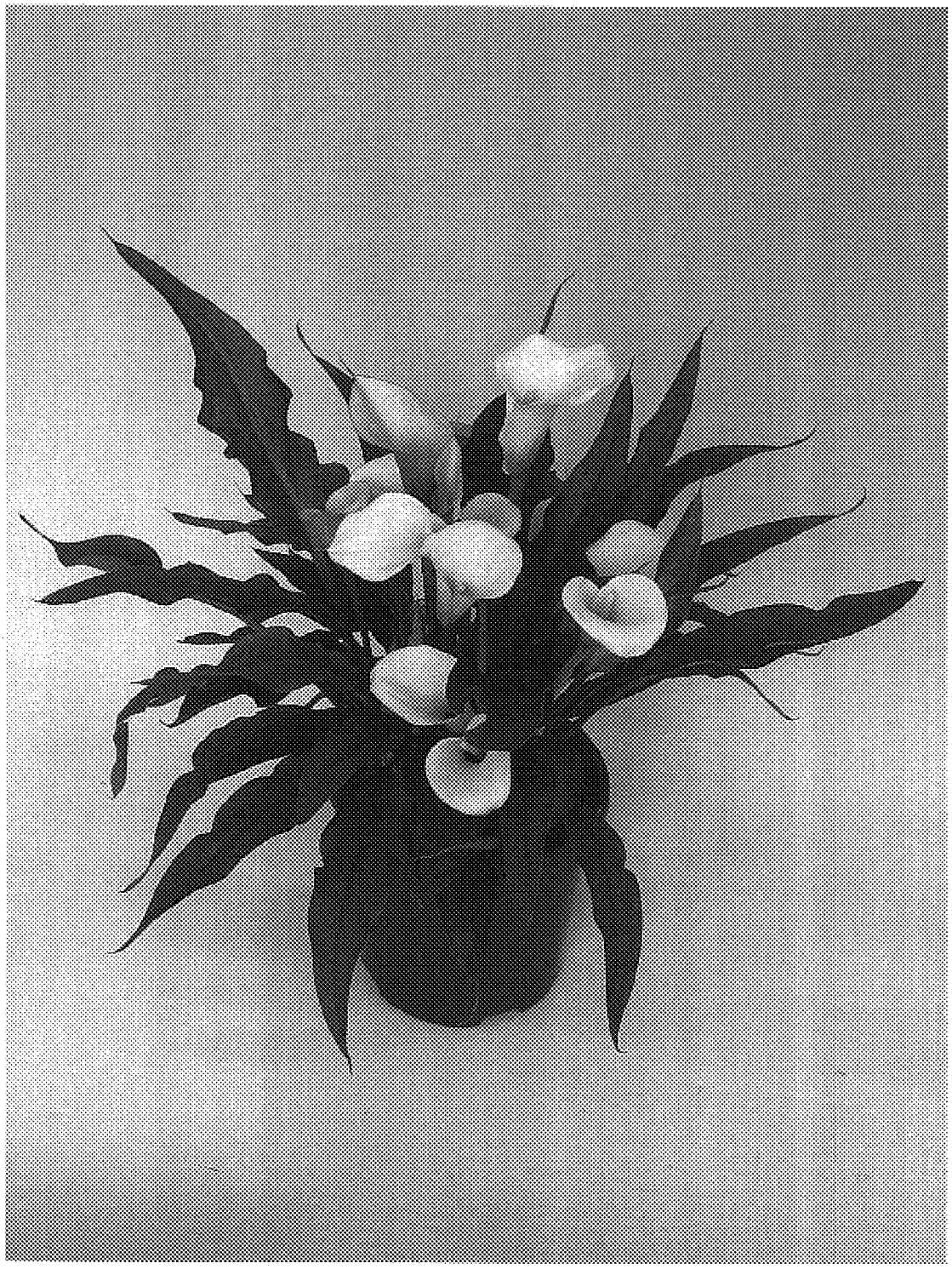

* * * * *